United States Patent [19]

Schmidt-Ott et al.

[11] Patent Number: 4,574,004
[45] Date of Patent: Mar. 4, 1986

[54] METHOD FOR CHARGING PARTICLES SUSPENDED IN GASES

[76] Inventors: Andreas Schmidt-Ott, 12 Am Holbrig; Hans-Christoph Siegmann, 24 Kurberstrasse, both of CH-8049 Zurich, Switzerland

[21] Appl. No.: 597,056

[22] Filed: Apr. 5, 1984

Related U.S. Application Data

[63] Continuation of Ser. No. 323,463, Nov. 20, 1981, abandoned.

[30] Foreign Application Priority Data

Oct. 28, 1980 [CH] Switzerland .................. 8002/80

[51] Int. Cl.[4] .................. B03C 3/12; B03C 3/38; H01J 27/24
[52] U.S. Cl. .................. 55/4; 55/102; 55/129; 55/138; 55/279; 250/423 P; 250/283; 250/503.1; 250/504 R; 422/121; 324/469
[58] Field of Search .................. 55/4, 102, 123, 128, 55/129, 138, 279; 422/121; 324/469; 250/283, 423 P, 503.1, 504 R; 313/231.71; 361/226

[56] References Cited

U.S. PATENT DOCUMENTS

| | | | |
|---|---|---|---|
| 2,418,339 | 4/1947 | Ehrgott | 55/102 |
| 2,593,869 | 4/1952 | Fruth | 55/102 |
| 2,868,317 | 1/1959 | Maas et al. | 55/102 |
| 2,898,800 | 8/1959 | Bergson | 55/102 |
| 2,943,134 | 6/1960 | Liao et al. | 55/102 |
| 2,959,677 | 11/1960 | Robinson et al. | 250/423 P |
| 3,476,968 | 11/1969 | Omura | 55/102 |
| 3,653,185 | 4/1972 | Scott et al. | 55/102 |
| 3,740,552 | 6/1973 | Pressman | 250/423 P |
| 3,853,750 | 12/1974 | Volsy | 55/123 |
| 3,948,625 | 4/1976 | Schultz | 55/102 |
| 3,987,302 | 10/1976 | Hurst et al. | 250/423 P |
| 4,254,336 | 3/1981 | Rustler | 250/423 P |
| 4,298,005 | 11/1981 | Mutzhas | 250/503.1 |
| 4,317,042 | 2/1982 | Bart et al. | 250/504 R |
| 4,377,749 | 3/1983 | Young | 250/423 P |
| 4,454,425 | 6/1984 | Young | 250/423 P |

FOREIGN PATENT DOCUMENTS

| | | | |
|---|---|---|---|
| 848687 | 9/1960 | United Kingdom | 55/102 |
| 1233915 | 6/1971 | United Kingdom | 324/469 |

OTHER PUBLICATIONS

Weaks, R. W. and Duley, W. W. Interaction of Tea CO$_2$ Laser Radiation with Aerosol Particles, Nov. 1976/vol. No. 11/Applied Optics, pp. 2917-2921.

Primary Examiner—David L. Lacey
Attorney, Agent, or Firm—Browdy and Neimark

[57] ABSTRACT

The invention concerns a method and apparatus for electrically charging particles of liquid or solid matter suspended in gases, especially in air. The particle carrying gas is irradiated with ultraviolet light having an energy below the threshold for ionization of the gas, but above the photoelectric threshold of the particles. The actual charging occurs by photoemission of electrons from the particles. The photoelectrons or negative small ions are removed from the neighborhood of the positively charged particles by diffusion to a charge absorbing surface. The photoelectric charging method and apparatus of the present invention are highly effective, particularly for very small particles and yields chemical information on the particles and their surface.

7 Claims, 5 Drawing Figures

METHOD FOR CHARGING PARTICLES SUSPENDED IN GASES

This is a continuation, of application Ser. No. 323,463, filed Nov. 20, 1981, now abandoned.

BACKGROUND OF THE INVENTION

Small particles of liquid or solid matter suspended in gases are of increasing importance in science and technology. In the air, such particles are a troublesome byproduct of combustion and other industrial processes, there exists, therefore, a need to remove them as completely as possible. In particular human generated aerosols are used in weather modification methods to act as nuclei for the condensation of ice crystals. Another example of use is in the production of smoked meat, where the particles are produced in a smoldering fire and have to be deposited onto the meat.

If the particles are charged electrically, it is possible:
(i) to remove them from the gas,
(ii) to measure their number and size distribution,
(iii) to deposit them at any desired location,
(iV) to influence their coagulation.

Such electrical charging has been achieved so far by first producing ions of positive or negative electrical charge in the gas via an electrical discharge, a radioactive source or other means, and letting the ions attach to the particles by diffusion. This diffusion charging is non-destructive, but it has the disadvantage of being very inefficient for ultrafine particles. In air for instance, particles with a diameter of less than $10^{-8}$ m cannot be charged with appreciable efficiency. Furthermore, diffusion charging depends only on the size of the particle and not on its chemical properties or the state of its surface. In nucleation, and in the catalysis of chemical reactions, it is the small particles and the adsorbate condition on their surface that is of crucial importance. Therefore, there is a need for a charging mechanism that allows charging of very small particles, and additionally distinguishes between particles of different chemical composition and surface properties. Also, the charging should be non-destructive and leave the particle surface and environment unchanged.

SUMMARY OF THE INVENTION

In view of the foregoing, it is the object of this invention to provide a method and an apparatus for electrically charging particles suspended in gases that
(1) operates for a range of particle sizes including very small particles,
(2) depends on the particle material and particularly on the chemicals adsorbed at the surface,
(3) is non-destructive,
(4) may be simple and inexpensive.

These and other objects of the invention are achieved by irradiating the gas containing the particles with ultraviolet light. The energy of the photons is chosen below the photoionization of the gas but above the photoelectric threshold $\Phi$ of the particles. Thus, the gas remains neutral whereas the particles emit photoelectrons. In some gases these photoelectrons will attach themselves to neutral gas molecules forming negative ions called small ions. The photoelectrons or small ions are removed from the neighborhood of the particles by providing a surface, for instance the wall of a container, that is large compared to the joint surface of the particles hit by the ultraviolet light. Under these conditions the photoelectrons or small ions are removed from the gas by diffusion to the surface where they are absorbed and eventually neutralized. The process of diffusion to the charge absorbing surface may further be influenced by external electrical fields. The particles are left behind with a positive electrical charge. There is of course a loss of particles because they also diffuse to the charge absorbing surface. However, the diffusion of the particles is much slower compared to the photoelectrons or small ions because of their larger mass.

The process of the photoelectric charging according to the present invention may be monitored by electrically insulating the charge absorbing surface and measuring the diffusion current flowing to it. The ultraviolet light may be pulsed or switched on and off periodically to allow phase sensitive detection of the diffusion current. Alternatively, one or two auxiliary electrodes may be introduced close to the illuminated region of the gas. If voltage, preferably an AC voltage, is applied between these electrodes, the electrical conductivity due to the small ions, or photoelectrons, and/or charged particles can be measured for monitoring the inventive photoelectric charging. The applied voltage is preferably an alternating voltage in order not to disturb the charge distribution.

The charge absorbing surface must be connected to a constant electric potential, and it must be conducting such that it does not charge up on absorbing the diffusion current. It also must not emit many photoelectrons itself, thereby increasing the density of a negative mobile charge in the illuminated region of the gas. Sufficient electrical conduction at low photoelectric yield exists in materials with high photoelectric threshold and/or low density of states at the highest occupied electron levels. Weakly doped insulators furnish ideal charge absorbing surfaces. If the photon energy is very high, photoemission from the charge absorbing surface can be reduced by avoiding direct exposure to the light.

There may also be two electrically insulated charge absorbing surfaces close to the illuminated region. If an AC voltage of sufficient magnitude is applied between these two surfaces, the photoelectrons or small ions will be extracted from the illuminated region and absorbed by the surfaces, whereas the less mobile positively charged particles will only perform a jitter of comparatively small amplitude and thus stay in the illuminated region. The application of the AC voltage increases the efficiency of the photoelectric charging according to the present invention.

The photoelectric charging according to the present invention may also be combined with the prior art diffusion charging in several ways. The combined charging may take place, for instance, within the photoelectric charging region itself by letting part of the photoelectrons or small ions reattach themselves to the particles. Additionally, the charge absorbing surface may be exposed directly to the ultraviolet light to produce photoelectrons itself. For this purpose, an auxiliary electrode of small surface may be introduced close to the illuminated region. A voltage which is positive with respect to the charge absorbing surface is applied to the auxiliary electrode. The photoelectrons produced by the charge-absorbing surface are drawn into the gas by the voltage applied to the auxiliary electrode. The relative loss of charged particles by diffusion to the charge absorbing surface is minimal, if a flow of the particle carrying gas is maintained.

A second important combination of diffusion charging and the photoelectric charging according to the present invention is achieved if the particles are first charged by attachment of electrons or negaive ions (diffusion charging), and subsequently enter the photoelectric charger according to the present invention. The particles with high photoemissivity will then be neutralized, whereas the particles with low photoemissivity will keep their negative charge.

The simultaneous photoelectric and negative diffusion charging leads to an increase of the positive charge on the particles with high photoemissivity and to an increase of the negative charge on the particles with low photoemissivity and/or high attachment coefficient for electrons or small ions. This separates the particles according to their size, state of surface and/or material, and energy of the ultraviolet light. In this way too, one can study the changes of particles in chemical reactions or extract certain particles from a mixture.

The application of the photoelectric charging according to the present invention is based on the recognition, that photoemission of electrons from small particles is different from photoemission from extended surfaces. The first step in the novel method of photoelectric charging is the absorption of the ultraviolet light by excitation of an electron in the particle. This step depends on the optical properties of the material. It has been discovered recently that there can be an enormous enhancement of optical absorption if the particle is small. This happens for instance in Ag-particles, where optical absorption is enhanced a hundredfold due to the enhanced electrical polarizability. The second step is the escape of the photoexcited electron over the surface barrier potentials. This step depends on the surface properties of the particle, in particular on the adsorbate situation. Small particles have an enhanced photoelectric yield compared to the larger ones. This situation arises as soon as the attenuation length of photoexcited electrons in the particle is comparable to the dimensions of the particle. Enhancement factors over plane surfaces of ~4 have been found for this process in particles of less than $10^{-8}$ m in diameter.

The third step according to the present invention is the escape of the photoelectron from the close neighborhood of the particle. Since there is a Coulomb attraction between the escaping photoelectron and the particle left behind, the effective work function is higher compared to the one of a plane surface. For a sphere with radius R the increase $\Delta\Phi$ of the work function is given by $(e^2/4\pi\epsilon_0 R) \cdot (p+\frac{3}{8})$, where e is the elementary charge, $\epsilon_0$ the dielectric constant of the vacuum and p the number of charges on the particle before photoemission. This step introduces a size dependence of the photoelectric threshold.

In the fourth step finally, the photoelectron thermalizes at a distance d from the particle. In some gases, in particular in air, this step is accompanied by the formation of a small ion since thermal electrons tend to attach themselves to neutral oxygen molecules. If the particle is very large, and/or if the cross sections of the gas molecules are such that d is short, and/or if the charge (p+1) on the particle is high, the photoelectron or small ion may diffuse back to the particle instead of reaching the charge absorbing surface. Hence, the fourth step introduces a gas, pressure, and temperature dependence of the inventive charging, besides an additional favoring of the smaller particles. Diffusion of the photoelectron back to the particle appears obvious from the prior art point of view. The recognition that it is not effective for a small particle is especially important for the operating of the particle charger according to the present invention.

The above considerations show that the inventive photoelectric charging of particles suspended in gases is highly effective for small particles, material and surface sensitive, and nondestructive. In the following description of the preferred embodiments it will become apparent that it also may be very simple and inexpensive.

The time $\tau$ during which the light is incident onto the particle carrying gas is important. $\tau$ must be adjusted either through the flow velocity of the particle carrying gas through the illuminated region, and/or by pulsing or interrupting the ultraviolet light, to achieve the desired charging conditions.

At small $\tau$ the charge generated on a particle of radius R is given by $$\sigma = \text{const } R^2 \cdot Y \cdot \tau \qquad \text{I}$$

The photoelectric yield Y is the number of photoelectrons emitted per incident photon. Y contains the desired information on the particle surface and bulk material. In some materials, Y may also show the forementioned enormous enhancement, especially for small particles.

At large $\tau$, the particles acquire a saturation charge $\sigma_\infty$ given by $$\sigma_\infty = f(R) \qquad \text{II}$$

where f(R) is a monotonic function over a large range of R. For the smallest particles, $\sigma_\infty \equiv 1$ is often a good approximation.

To study, for instance, the catalytic activity of the particles, or to monitor chemical reactions, or to investigate nucleation processes, for instance, in artificial weather methods modification, one needs to know the photoelectric charge, or the spectrum of photoelectric charges attached to each particle size in the photoelectric charger according to the present invention operated in conditions described by equation I or II.

According to the prior art the charge $\sigma$ can be measured by letting the gas flow stream through a filter in an insulated Faraday cage connected to a current meter. Another well-known technique yields the charge and the electrical mobility of the particle to which this charge is attached. In the latter method one lets the gas flow stream through one or several cylindrical condensers. The current flowing to the negative electrode is measured as a function of the voltage across the condenser(s). Prior art refinements of this method to improve the resolution and to reduce the time needed for taking a mobility spectrum of the particles include the addition of a sheath of particle free gas and the subdivision of the negative electrode into several pieces, where the current deposited on each section is measured separately.

If these prior art techniques are combined with the photoelectric charging according to the present invention, one obtains the charge $\tau$ for each electrical mobility. One can also remove part or all of the particles that have been charged.

However, in the case of a complex spectrum of particles with various surface and material properties, one needs to combine the photoelectric charging according to the present invention with the prior art diffusion charging plus subsequent mobility analysis. One procedure may be as follows: First, the gas containing the particles flows through an inventive photoelectric charge, and then through a cylindrical condenser, in which part of the particles is precipitated according to the voltage across the condenser and the charge on the particles. Thereafter, the gas enters a prior art neutralizer, in which a radioactive source creates small ions of either sign which diffuse to the particles thus neutralizing any remaining charge. Finally, the particle carrying gas flows for instance into a commercial electrical aerosol analyzer as, for example, Withby Electrical Aerosol Analyzer for obtaining the number of particles as a function of particle size the comparison of these particles spectra with the ultraviolet radiation turned on and off in the photoelectric charger of the present invention at various voltages across the subsequent cylindrical condenser. This yields the number of particles of each size and their photoelectric charge $\sigma$. The advantages of the photoelectric charging according to the present invention are that it is highly effective, especially for very small particles, and yields chemical information on the surface of the particles. Important applications exist in the control of nucleation and catalytic processes, in the measurement and analysis of aerosols, and in the size and material dependent removal or deposition of particles.

BRIEF DESCRIPTION OF THE DRAWINGS

Further objects and advantages of the present invention and its operation will become apparent from the following description in connection with the drawings in which.

DESCRIPTION OF THE PREFERRED EMBODIMENTS

Figure 1:
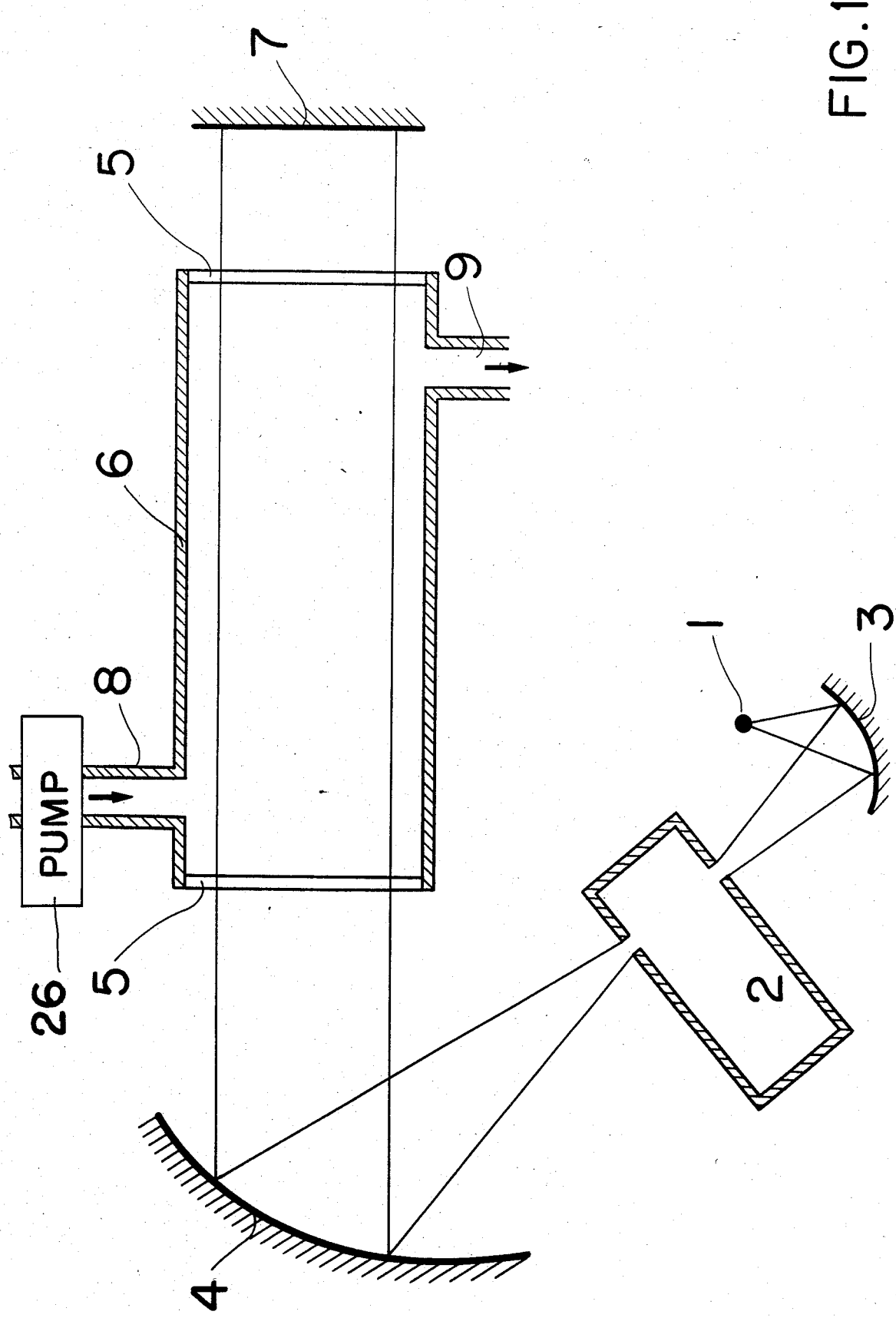
FIG. 1 is the embodiment of an inventive photoelectric charger using monochromatic light; the photon energy can be chosen at will.

Reference is now made to FIG. 1. The light from a high pressure arc, or a hydrogen discharge, or a synchrotron radiation source, or any other source of ultraviolet light 1 is focused onto the entrance slit of a monochromator 2 by a mirror 3. The monochromatic light emerging from the monochromator 2 is focused into a nearly parallel beam by mirror 4. Via the ultraviolet transmitting windows 5, the beam permeates the container 6. To increase the light intensity in the container 6, the beam may be reflected back by mirror 7. The gas with the particles flows into the container 6 through opening 8 and leaves the container 6 through opening 9. A pump or fan 26 may be interposed near opening 8 to maintain and suitably vary the flow rate of the particle carrying gas. The interaction time of the particles with the light is regulated by adjusting the flow velocity of the gas. The metallic walls of container 6 may be coated for instance with a very thin film of Silicone lacquer to reduce photoemission from these walls caused by stray light. By means of the monochromator 2, detailed studies of the bulk and surface properties of the particles may be performed over a wide range of photon energies and the photoelectric threshold may also be determined accurately, by measuring the charge created on the particles in this embodiment of the inventive photoelectric charger.

Figure 2:
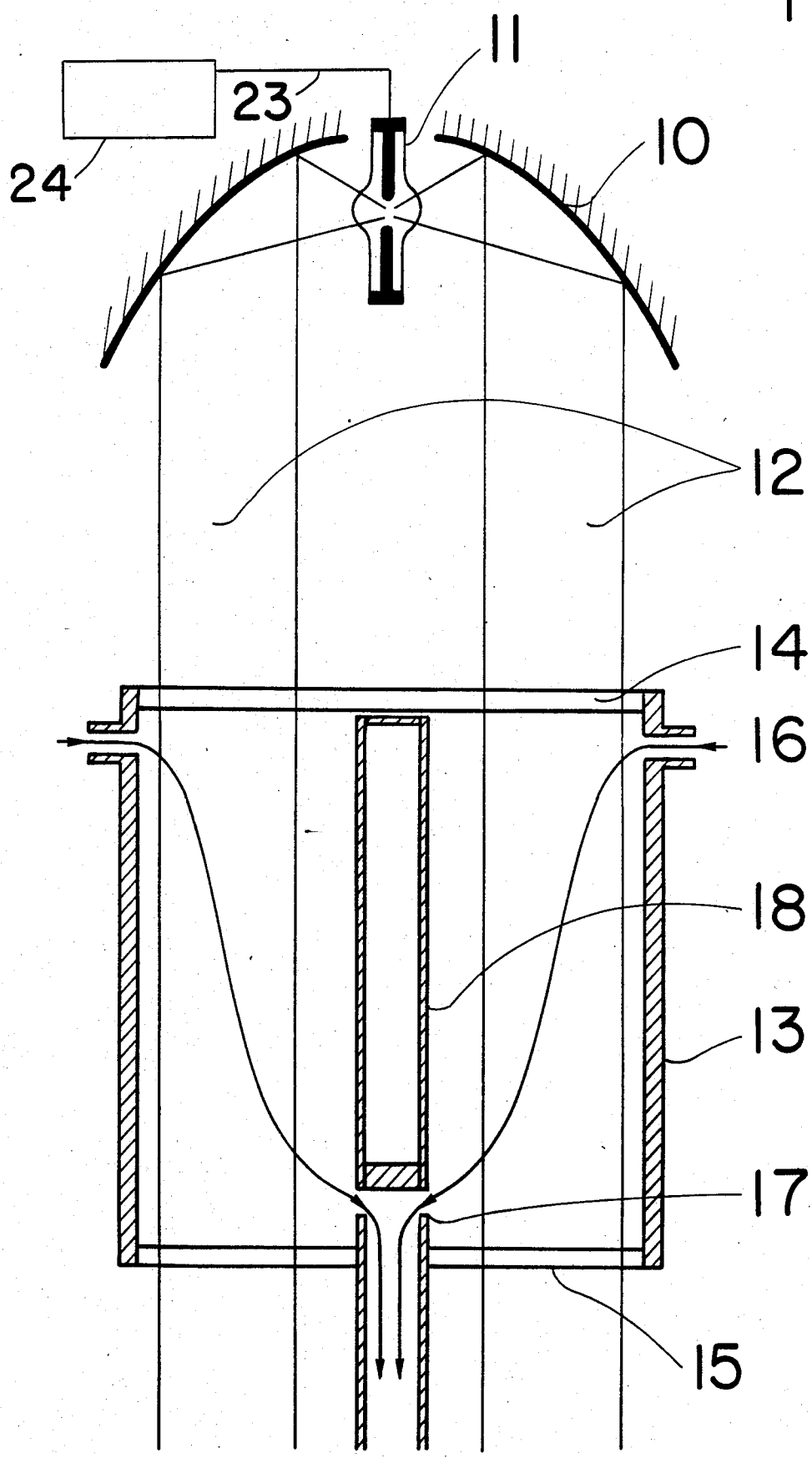
FIG. 2 is the embodiment of an inventive photoelectric charger using a pulsable high intensity light source for charging particles with comparatively high ionization threshold.

Reference is now made to FIG. 2. By means of a parabolic mirror 10, the light from a high pressure arc 11 is collected into a parallel hollow beam 12 permeating the container 13 through the UV transmitting windows 14 and 15. The particle carrying gas enters the container 13 via the annular opening 16 and leaves via holes 17 distributed regularly on the inner cylinder 18. The cylinder 18 is located in the light free part of the beam and is electrically insulated. An AC or DC voltage may be maintained between cylinder 18 and the container 13 to influence the diffusion of the small ions or photoelectrons to the charge absorbing surface, which is the inner wall of container 13. Additionally, cylinder 18 and container 13 may serve as electrodes to measure the electrical conductivity in the particle carrying gas to monitor the inventive photoelectric charging. This embodiment of the inventive photoelectric charger is designed for maximum light intensity. It allows the achievement of the conditions of equation II, in which the saturation charge is generated on the particles even if they possess very high photoelectric thresholds. Especially in the case of particles floating in air, it may be important to pulse the high pressure arc 11. Because of the higher temperature of the plasma permissible in pulsed operation, the output of photons with very high energy is increased. Further, the gas to particle reactions occurring in moist air for wavelengths shorter than 230 nm do not influence the surface properties of the particles under investigation if each filling of the container 13 receives one short light pulse only. This may be accomplished by any suitable pulsing means 24 connected to arc 11 by means of an electrical connection 23. The flow of the particle carrying gas through the photoelectric charger is adjustable, and the charge absorbing surfaces may be treated for minimal photoemission.

Figure 3:
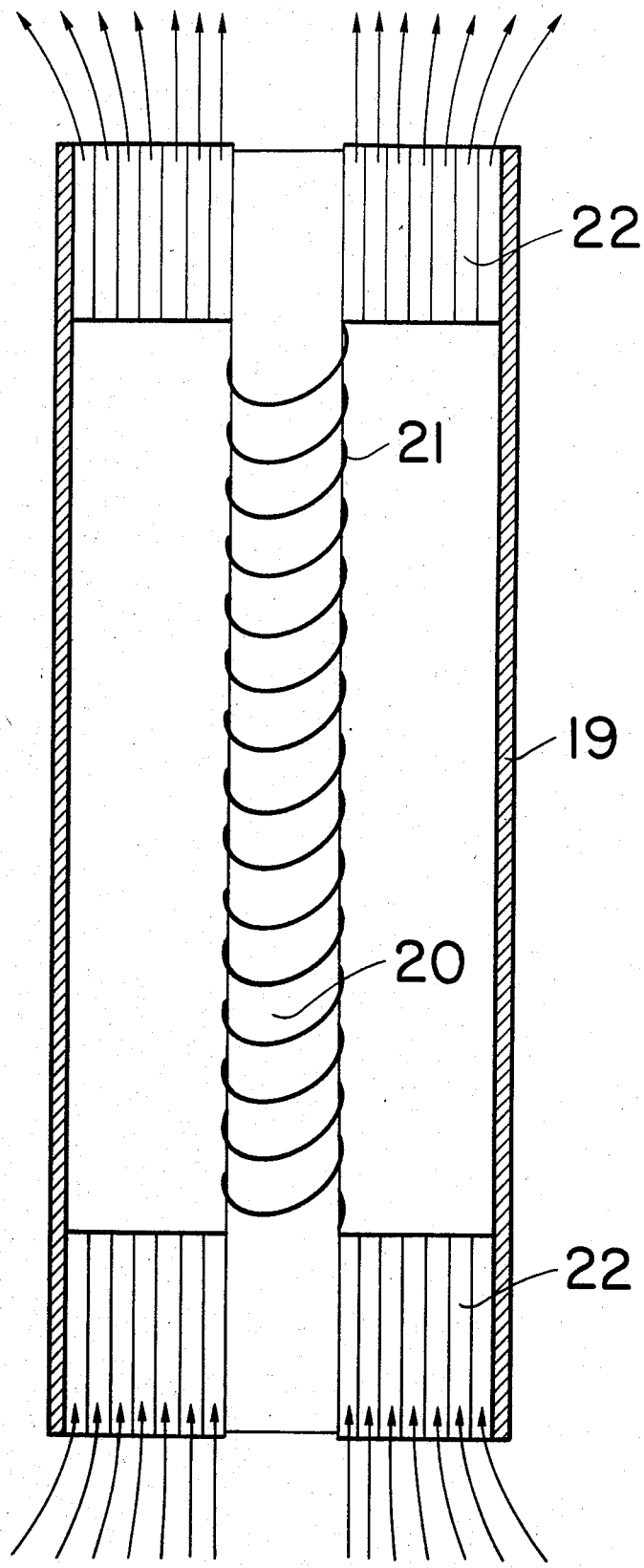
FIG. 3 is the most simple embodiment of an inventive photoelectric charger using a monochromatic low pressure discharge lamp as the light source.

Reference is now made of FIG. 3. The container 19 is a tube, the inner surface of which constitutes the charge absorbing surface treated for minimal photoemission. The light source 20 is a commercial low pressure mercury discharge lamp as used for sterilization. It yields monochromatic light of a wave length of 252 nm which is below the threshold of ozone formation. The electric fields generated in the low pressure discharge are screened by a wire or wire mesh 21 encircling the lamp. In this way, it is possible to maintain an AC or DC electric field between light source 20 and container 19 to influence the diffusion of the small ions or photoelectrons to the charge absorbing surface of the inner surface of container 19 , or to monitor the process of the inventive photoelectric charging by observing the electrical conductivity of the particle carrying gas. The light source 20 is held in the axis of container 19 by supports 22 with many channels to promote laminar flow of the particle carrying gas and to stop the ultraviolet light from exiting the container 19. The walls of channels in support 22 may also be coated with a light absorbing paint. The appropriate flow of the particle carrying gas through the inventive photoelectric charger is maintained by a fan or pump (not shown) mounted on top of the device or by mounting the axis of the container 19 with light source 20 vertically such that the air flow is maintained as in a chimney by the heat generated in the lamp. In this case, the size of the channels in the support 22 must be chosen such that the velocity of the flow is appropriate for the desired charging conditions. If a DC voltage is maintained between the wire 21 and the container 19, with the positive pole at wire 21, the charged particles will be precipitated at container 19. The inventive photoelectric charger then simultaneously acts as an air purifier. Additionally, any bacteria and viruses floating in the air are killed by the ultraviolet light. If the gas is heavily loaded with particles, it may however be advantageous to apply the DC voltage to a subsequent cylindrical condenser, where the charged particles are precipitated. This subsequent condenser can be cleaned more easily or discarded if contaminated with particles.

Figure 4:
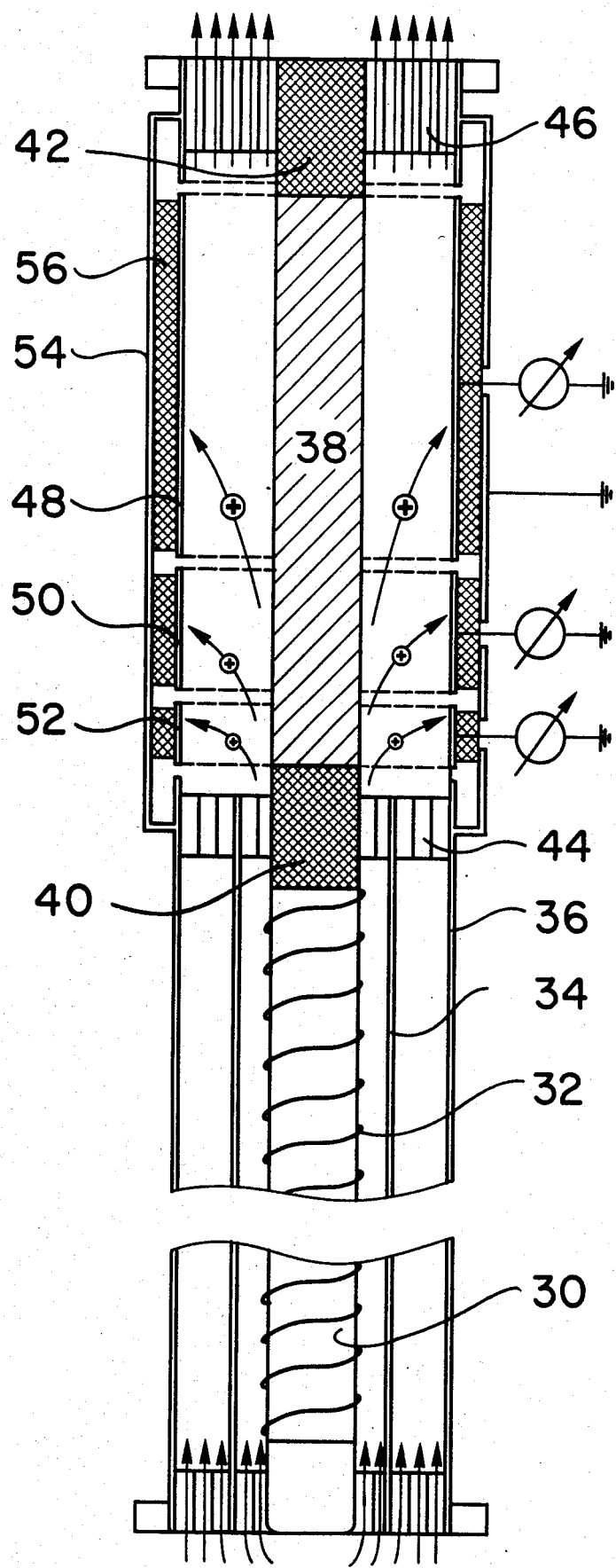
FIG. 4 illustrates a combination of the inventive photoelectric charger with a prior art cylindrical condenser for taking the mobility spectra of the particles charged by the inventive method.

Reference is now made to FIG. 4, which shows a combination of the photoelectric charger according to the present invention with a prior art cylindrical condenser for analyzing the electrical mobility of the charged particles. A light source 30 is electrically screened by a wire 32, and is mounted in the axis of a cylindrical container 34 whose inner wall is the charge absorbing surface. An AC voltage may be applied between wire 32 and container 34. This photoelectric charger of the type displayed in FIG. 3 in more detail, is mounted coaxially in a tube 36. The particle carrying gas flows both through the space between the light source 30 and container 34 and through the space between container 34 and container 36. However, the particles carried in the latter flow are not charged photoelectrically. Both gas flows subsequently enter the analyzing cylindrical condenser. The inner electrode 38 of this condenser is held coaxially to the light source 30 by insulators 40 and 42 and by perforated supports 44 and 46. The inner electrode 38 is metallic and carries a positive voltage against the outer electrodes 48, 50 and 52 which are co-axial electrically insulated metallic tubes connected to current meters. An outer tube 54 carries insulators 56 that hold tubes 48, 50 and 52 in place and screens them electrically.

If a laminar gas flow is maintained through the device by an adjustable fan or a pump (not shown), the particles charged in the photoelectric charger will be precipitated on electrodes 48, 50, or 52 according to their electrical mobility. The current neutralizing the electrical charge associated with the precipitation of the particles will be indicated in the meters. In this way, the charge generated photoelectrically can be measured for each particle mobility simultaneously. This yields information on the size dependence of the photoelectric yield if the charger is operated in the condition of equation I or on the size spectrum of the photoelectrically active particles if the charger is operated in the condition of equation II. It may be necessary to remove all previously charged particles by letting the particle carrying gas first flow through an additional cylindrical condenser with a DC voltage before it enters the device shown in FIG 4.

Figure 5:
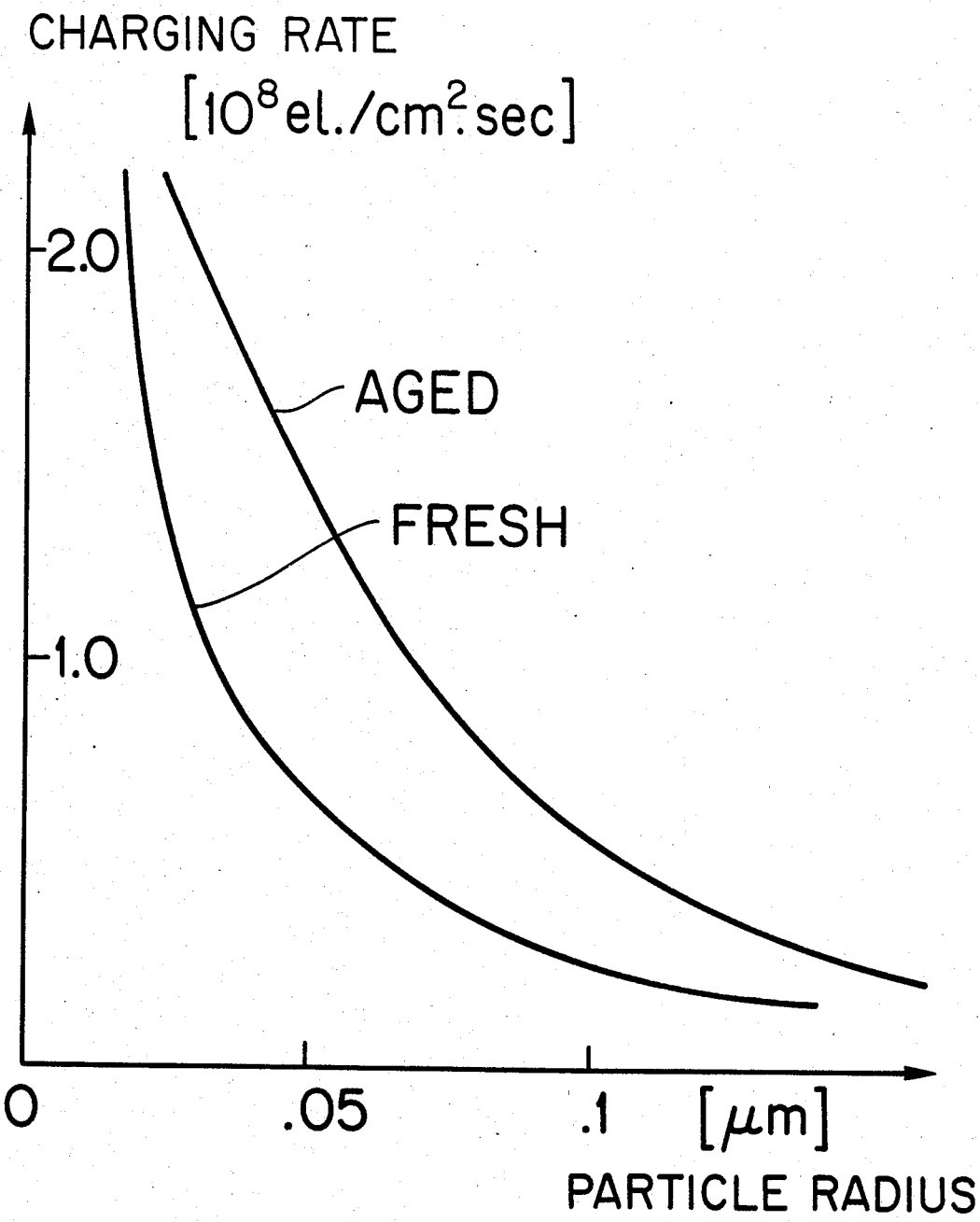
FIG. 5 shows the photoelectric charging rate per unit surface area of a fresh and aged aerosol created by automobile exhaust.

Reference is now made to FIG. 5 which shows the results of a measurement of the photoelectric charging rate on a car exhaust aerosol. A sample of this aerosol was measured both immediately and after aging for a few hours in a garage. The charging rate per unit particle surface is plotted vs the particle radius as determined by the commercial aerosol analyzer. It is evident that small particles are charged very efficiently by the photoelectric charger according to the present invention. It is also evident that changes in the adsorbate situation on the surface of the particles that occur upon aging, can be detected by the increase in the photoelectric yield.

Since many changes could be made in the above constructions and many apparently widely different embodiments of this invention can be made without departing from the spirit and scope thereof, it is intended that all matter contained in the above description or shown in the accompanying drawings shall be interpreted as illustrative and not in a limiting sense.

What is claimed is:

1. A method for electrically charging small particles suspended in a gas, in a material and surface sensitive, non-destrictuve manner, comprising the steps of:
    irradiating a gas containing small particles in suspension by exposing the gas to ultraviolet radiation of photon energy above the photo-threshold of the particles and below the ionization threshold of the gas to generate, substantially solely by photoemission of electrons from the particles, positively charged particles, photoelectrons, and negatively charged small ions formed by attachment of photoelectrons to gas molecules;
    absorbing and neutralizing diffused photoelectrons and small ions by absorption onto a charge absorbing surface having a constant electric potential and a sufficient surface conductivity at a low photoelectric yield to avoid charge buildup and increase of negative mobile charge, and
    causing the charged particles to remain in the vicinity of the charge absorbing surface for a time insufficient to permit substantial precipitation of the positively charged particles at said surface.

2. The method of claim 1, further including the step of measuring the electrical conductivity of the particle-carrying gas in the region in which it is being irradiated.

3. The method of claim 1, further including the step of diffusion-charging the particles.

4. The method of claim 3, wherein the particles are diffusion charged before said irradiating step.

5. The method of claim 1, further including the step of precipitating the charged particles, after the particles have emerged from the vicinity of the charge absorbing surface.

6. The method of claim 5, wherein the charged particles have been exposed to diffusion charging before being precipitated.

7. The method of claim 1, further including the step of selecting the range of ultraviolet light with a monochromator.

* * * * *